(12) United States Patent
Coughlin et al.

(10) Patent No.: US 6,423,675 B1
(45) Date of Patent: Jul. 23, 2002

(54) CLEANING-IN-PLACE COMPOSITION AND METHOD FOR USING THE SAME

(75) Inventors: Michael Francis Coughlin; David Christopher Cole, both of Cincinnati; Charles Allen Crawford, Maineville, all of OH (US)

(73) Assignee: Diversey Lever, Inc., Plymouth, MI (US)

( * ) Notice: Subject to any disclaimer, the term of this patent is extended or adjusted under 35 U.S.C. 154(b) by 0 days.

(21) Appl. No.: 09/447,644

(22) Filed: Nov. 23, 1999

(51) Int. Cl.$^7$ .............. C11D 3/22; C03C 23/00; C23G 1/00; B08B 3/00

(52) U.S. Cl. .............. 510/234; 510/218; 134/2; 134/26

(58) Field of Search .............. 510/218, 234; 134/2, 26

(56) References Cited

U.S. PATENT DOCUMENTS

| | | | |
|---|---|---|---|
| 2,392,936 A | * 1/1946 | Mattin et al. | 252/187 |
| 4,432,856 A | * 2/1984 | Murakami et al. | 204/237 |
| 4,542,008 A | * 9/1985 | Capuano et al. | 423/477 |
| 4,889,654 A | 12/1989 | Mason et al. | |
| 5,064,561 A | * 11/1991 | Rouillard | 252/174 |
| 5,078,967 A | 1/1992 | Riera Aixala | |
| 5,324,477 A | 6/1994 | Schroeder et al. | |
| 5,533,552 A | * 7/1996 | Ahlers | 141/144 |
| 5,567,444 A | * 10/1996 | Hei et al. | 424/616 |
| 5,770,555 A | * 6/1998 | Weinstein | 510/434 |
| 5,888,311 A | * 3/1999 | Laufenberg et al. | 134/10 |

FOREIGN PATENT DOCUMENTS

| | | |
|---|---|---|
| EP | 347 320 | 12/1989 |
| GB | 2 313 369 | 11/1997 |
| WO | 93/17960 | 9/1993 |
| WO | 98/38865 | 9/1998 |

OTHER PUBLICATIONS

International Search Report dated Feb. 28, 2001.
Abstract from Database FSTA–*The Growing Use of Chlorine Dioxide*, Elphick A.
Abstract from Database WPI, Section Ch, Week 199840, Derwent Publications Ltd., London GB; JP101972377 (Chisso Corp.).
Abstract from Database WPI, Section Ch, Week 199847, Derwent Publications Ltd., London GB; JP63248896 (Makino A.).
Abstract from Database FSTA–*Developments in Detergents and Disinfectants*, Grimmett C.

* cited by examiner

*Primary Examiner*—Yogendra N. Gupta
*Assistant Examiner*—John M Petauncio
(74) *Attorney, Agent, or Firm*—Edward A. Squillante, Jr.

(57) ABSTRACT

A composition for a cleaning-in-place system is described. The composition has a halogen dioxide and a optionally hydroxide and does not require the use of a detergent to display excellent cleaning and disinfecting properties on processing equipment such as the equipment found in breweries, dairy plants and carbonated beverage plants.

6 Claims, No Drawings

CLEANING-IN-PLACE COMPOSITION AND METHOD FOR USING THE SAME

FIELD OF THE INVENTION

This invention is directed to a composition employable in a cleaning-in-place (CIP) system. More particularly, the invention is directed to a CIP composition that cleans, disinfects or both without requiring the use of a detergent. Also, described herein is a method for using such a CIP composition.

BACKGROUND OF THE INVENTION

It is extremely important to clean food processing facilities like breweries, dairy plants and carbonated beverage plants. Typically, such food processing facilities are cleaned by subjecting the internal or external portions of the machines that make up the facilities to a solution that reacts with the various soils present within the machines.

A conventional CIP system, for example, has several storage containers. Each storage container, independently, houses a solution (e.g., pre-rinse solution, cleaning solution, post-rinse solution) that is fed (non-simultaneously) into the facility targeted for cleaning or decontamination. Often, the solutions are pumped into the gas and liquid passages of the machines in the facilities being cleaned and then circulated through the system until they are finally discharged to waste.

Typical CIP systems are known to employ chlorine. However, chlorine is not environmentally friendly and can form by-products with many organic substances found in the facilities being cleaned. These by-products are not desired and can be carcinogenic materials. Also, chlorine may result in carcinogenic by-products in, for example, the waste sites it is finally discharged to. Other CIP systems are known to use active agents like hydrogen peroxide and peracetic acid. Such systems, however, require high levels of the active agents making their uses non-feasible, for example, from an economic standpoint. Furthermore, agents like peracetic acid tend to have a very pungent aroma.

It is of increasing interest to prepare a CIP composition that is environmentally friendly and economical to use. This invention, therefore, is directed to a CIP composition that does not result in the generation of environmentally unfriendly by-products and that unexpectedly does not require the use of a detergent to demonstrate superior cleaning properties. This invention is also directed to a method for using the CIP composition in a food processing facility.

BACKGROUND REFERENCES

Efforts have been disclosed for cleaning processing equipment. In U.S. Pat. No. 5,888,311, a process for cleaning equipment in the absence of a pre-rinse step is described.

Other efforts have been disclosed for cleaning equipment. In U.S. Pat. No. 5,533,552, a CIP process comprising the step of circulating a cleaning liquid throughout equipment targeted for cleaning is described.

Still other efforts have been described for cleaning equipment. In U.S. Pat. No. 5,064,561, a two part CIP system is described and the system utilizes an alkaline material and an enzyme.

SUMMARY OF THE INVENTION

In a first embodiment, this invention is directed to a CIP composition comprising a halogen dioxide, wherein the halogen dioxide is derived from a precursor alkali metal halite or alkaline earth metal halite, or both.

In a second embodiment, this invention is directed to a method for cleaning or disinfecting processing equipment with the CIP composition described in the first embodiment of this invention.

In a third embodiment, this invention is directed to a method for cleaning and disinfecting processing equipment with the CIP composition described in the first embodiment of this invention.

In a fourth embodiment, this invention is directed to processing equipment comprising, internally, the CIP composition of this invention or processing equipment coated with the CIP composition of this invention, or both.

DETAILED DESCRIPTION OF THE PREFERRED EMBODIMENTS

Regarding the halogen dioxide used in the CIP composition of this invention, such a compound preferably comprises fluorine, and most preferably, comprises chlorine, with chlorine dioxide being especially preferred. The halogen dioxide is typically prepared by subjecting an alkali metal halite to an acid, like sulfuric acid.

Preferably however, the halogen dioxide is prepared by mixing a precursor with water and supplying current. The precursor added to the water is preferably an alkali metal halite, an alkaline earth metal halite, or both. The amount of precursor added to the water is generally from about 1.0% to about 30.0%, and preferably, from about 2.0% to about 20.0%, and most preferably, from about 3.0% to about 7.0% by weight precursor, based on total weight of precursor and water, including all ranges subsumed therein.

The water that is mixed with the precursor may be tap water and is preferably soft water. The soft water preferably comprises substantially no calcium, magnesium and iron, and does comprise from about 10 ppm to about 5000 ppm, and preferably, from about 15 ppm to about 1000 ppm, and most preferably, from about 50 ppm to about 500 ppm sodium, based on total parts of the sodium and soft water, including all ranges subsumed therein.

The CIP composition of this invention is typically produced by any conventional techniques capable of generating a halogen dioxide. Preferably, however, the CIP composition is produced in a commercially available halogen dioxide generator such as those sold under the name of OXYCHLORe- by International Dioxcide. This method is desired because it allows for the generation of halogen dioxide without requiring the addition of an acid. When preparing the composition, the precursor (e.g., Sodium Chlorite) and soft water solution reacts with electricity yielding the following reaction (composition):

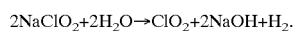

$$2NaClO_2 + 2H_2O \rightarrow ClO_2 + 2NaOH + H_2.$$

The resulting composition is an illustrative example of the CIP composition which may be used in this invention. The preferred precursor solution is anthium dioxide and made commercially available from International Dioxcide.

The amount of current supplied is limited only to the extent that halogen dioxide may be produced. Often, however, a 110 volt alternating current system is used whereby the system tends to deliver from about 10 to 20 amps of current.

When preparing the CIP composition of this invention, temperature and pressure may be maintained at any level that results in halogen dioxide generation. Preferably, however, the temperature is ambient and the pressure is atmospheric.

It is noted herein that the CIP composition of this invention unexpectedly displays both detergent and disinfectant properties when maintained in the pH range from about 6.0 to about 8.0. When superior cleaning properties are desired, the composition is maintained at a pH from about 7.0 to about 14.0, and preferably, from about 7.2 to about 13.0, and most preferably, from about 8.0 to about 10.0, including all ranges subsumed therein. When superior disinfectant properties are desired, the composition is maintained at a pH from about 1.0 to about 6.9, and preferably, from about 2.0 to about 6.0, and most preferably, from about 4.5 to about 5.5, including all ranges subsumed therein. Surprisingly, superior cleaning properties are obtained in the absence of a detergent. Superior cleaning and superior disinfectant properties are defined by the data present in the tables below.

The pH of the CIP composition of this invention may be modified by optionally adding acids, bases and/or employing buffers. Such acids include sulfuric and phosphoric acid. The bases include sodium, potassium and lithium hydroxide and the buffers include bicarbonate, carbonate and bicarbonate/carbonate buffers and borax. The amount of pH modifiers that may be used is limited only to the extent that the desired pH is obtained. As to the buffers, the amount added is enough to keep the CIP composition of this invention substantially stable. Regarding the bases, such bases may be generated directly within the process for synthesizing the halogen dioxide. This is often the case when the Oxychlor e-generator is used wherein the base (e.g., NaOH) may remain in the CIP composition or be drawn off.

After the CIP composition of this invention is prepared, the pH of the CIP composition may be modified or buffered in the tank generator it is prepared in. Optionally, a separate tank may be used to modify or buffer the composition.

Subsequent to pH modifying and/or buffering, the CIP composition is pumped, via a pump and feed line, to the processing equipment targeted for cleaning, disinfecting or both. To extent possible, the CIP composition is pumped through all internal portions of the equipment until it is finally discharged for recycling or waste. Moreover, the CIP composition of this invention may be pumped or sprayed on to the external surface of the equipment targeted for cleaning or disinfecting. The pumping is achieved via any art recognized pump. Such pumps may generally be classified as peristaltic, diaphragm or positive displacement pumps. The pumps are typically manufactured by suppliers like Watson-Marlow, Inc. and Tri-Clover, Inc. The spraying devices which may be used, for example, to spray the external portion of the processing equipment are typically distributed through establishments like System Cleaners A/S. The pumps and spraying devices which may be used in this invention may also be purchased from sanitary and hygiene specialists like DiverseyLever. Moreover, it is within the scope of this invention to make and store the CIP composition of this invention and use the composition as needed. It is also within the scope of this invention to make the CIP solution and to then feed the CIP solution directly to the pump responsible for delivering the composition. Still further, a combination of stored and newly made CIP composition may be fed to the pump responsible for delivering the composition.

As to the conduit that may be employed in this invention, such conduit is limited only to the extent that it is capable of transporting the CIP composition of this invention. The conduit is often a polymeric conduit or metal conduit, with stainless steel being especially preferred. Also, such conduit has an inside diameter ranging from about 0.25 cm to about 20 cm, but preferably, is from about 2.5 cm to about 10 cm.

The rate at which the CIP composition is delivered to the processing equipment is limited only to the extent that the rate does not prevent the CIP composition from cleaning and/or disinfecting the processing equipment targeted. Typically, however, the rate at which the CIP composition is delivered to the processing equipment is one which is selected or derived from maintaining a minimum linear velocity from about 1.5 to about 2.5 meters/second.

When the CIP composition is supplied to the processing equipment, one composition may be supplied having a single pH. It is also within the scope of this invention, however, to supply a CIP composition of a first pH followed by a CIP composition having a second pH. The alternating of CIP compositions having different pH values is often preferred when conditions of maximum cleaning and maximum disinfecting are desired.

The supplying of the CIP composition of this invention to processing equipment targeted for cleaning and/or disinfecting may be done in a manner such that the composition is fed into a single feed line of the processing equipment. In a preferred embodiment, the composition is fed into a feed line of each component of the processing equipment. A superior method for feeding solutions through a multitude of feeding lines in processing equipment may be found in Docket No. 99-0420-UNI (filed concurrently herewith), commonly assigned to DiverseyLever, the disclosure of which is incorporated herein by reference.

It should be noted herein that the CIP composition of this invention comprises halogen dioxide and a hydroxide. It is, however, within the scope of this invention for the composition to consist essentially of halogen dioxide, hydroxide and water. It is further within the scope of this invention for the composition to consist of halogen dioxide, hydroxide and water. Moreover, when the CIP composition of this invention is pumped and/or sprayed, the CIP composition may be subjected to pressure and heat. Pressure and heat (e.g., temperature of the CIP composition) may vary and are only limited to the extent that the CIP composition may be used to clean and/or disinfect the processing equipment of concern.

The examples which follow below are provided to further illustrate and facilitate an understanding of the present invention. Therefore, the examples are not meant to be limiting and modifications which fall within the scope and spirit of the claims are intended to be within the scope and spirit of the present invention.

EXAMPLE 1

A 1 liter flask was charged with about 10.42 mL of anthium dioxide (5% Sodium Chlorite) as made commercially available by International Dioxide. About 3.2 mL of 1N $H_2SO_4$ were subsequently added to produce a solution having a pH of about 2.2. Deionized water was then added to produce 1 liter of total solution. The resulting chlorine dioxide solution (about 60% completion, 300 ppm) was used in the experiments which follow.

EXAMPLES 2–6

For each of the five (5) experiments below, two quartz UV cells having a path length of 5.0 cm were each charged with 5.95 mL of a 0.1 molar sodium phosphate solution (to establish a buffered pH of about 11). The first cell was further charged with 0.6 mL of neat (conventional) root beer, as made commercially available. The second cell was further charged with 0.6 mL deionized water. Both cells were then charged in a manner set forth in Table I below. Using the contents of the second cell as the blank, the absorbance of the resulting root beer solution was determined over the range of 440 to 700 nm, using a Hewlett-Packard 8452 UV/vis spectrophotometer. The absorbance over this wavelength range was integrated, and the percent (%) reduction in color of root beer was based on a comparison to the integrated absorbance of the control to which no CIP composition has been added.

TABLE I*

| Example | CIP Composition | Ppm | Ppm as | % Reduction of Color |
|---|---|---|---|---|
| 2 (Control) | None | — | — | 0.0 |
| 3 | 2.0 mL of 300 ppm solution from Example 1 + 3.45 mL $H_2O$ | 50 | Chlorine dioxide | 56.09 |
| 4 | 145 µL sodium hypochlorite solution (3.5%) + 5.31 mL $H_2O$ | 200 | Total chlorine | 36.49 |
| 5 | 26 µL hydrogen peroxide solution (30%) + 5.42 mL $H_2O$ | 300 | Active oxygen | 4.94 |
| 6 | 49 µL of peroxyacetic acid solution (35%) + 5.40 mL of $H_2O$ | 300 | Active oxygen | 25.76 |

*The data in Table I above depicts (as color reduction) the superior and unexpected cleaning properties obtained when using chlorine dioxide in a simulated cleaning-in-place experiment. Further, these unexpected cleaning properties were obtained in the absence of a detergent.

EXAMPLES 7–12

Examples 7–12 are provided to demonstrate the superior disinfecting properties of the CIP composition of this invention. The examples were carried out in a manner set forth in Table II which follows:

microbes in suspension was estimated by its serial dilution in Butterfield's phosphate buffer and subsequent transfer of 0.1 ml of the dilution series into a Petri plate containing the appropriate agar growth medium. The inoculated Petri plates were incubated for 48–72 hours (at about 37° C.) and the resulting colonies counted with a Quebec colony counter. The number of colonies on the Petri plates multiplied by the serial dilution factor is equal to the number of microbes in 0.1 ml of inoculum.

Number of Survivors in the Presence of CIP Composition

Suspension test: 1 ml of each microbial suspension was mixed with 9 ml of each CIP composition containing 50 ppm $CaCO_3$ at 10/9 of the recommended use concentration (RUC) so that final concentration was exact RUC. After contact times described above, 1 ml of the mixture was put to 9 ml of neutralizer[2] from which 0.1 ml of sample was plated onto the appropriate agar and incubated at 28° C. for 48–72 hours before counting. The number of colonies present on the Petri plates multiplied by the serial dilution factor is equal to the number of microbes in 0.1 ml that survived in the sanitizer solution.

Per Cent Microbes Killed by CIP Composition

The per cent microbes killed by CIP composition is calculated by using the following equation:

TABLE II***

| | | Cultures | | | | | |
|---|---|---|---|---|---|---|---|
| Example** | CIP Composition/ Concentration | Lactobacillus brevis | Bacillus cerus | Candida Albicans | Zygosaccharomyces bailii | Rhizopus stolonifer | Byssochlamys nivea |
| 7 | Aqueous chlorine dioxide/about 15 ppm | About 9.9999 | About 9.9999 | About 9.9999 | About 9.9999 | About 99.99 | About 99.99 |
| 8 | Mixed halogen/about 25 ppm | About 99.9999 | About 99.9999 | About 99.9999 | About 99.9999 | About 99.99 | About 99.99 |
| 9 | Peroxyacetic acid/about 125 ppm | About 99.9999 | About 99.99 | About 99.99 | About 99.99 | <99 | About 99.9 |
| 10 | Aqueous chlorine dioxide/about 15 ppm | About 99.9999 | About 99.9999 | About 99.9999 | About 99.9999 | About 99.9999 | About 99.9999 |
| 11 | Mixed halogen/about 25 ppm | About 99.9999 | About 99.9999 | About 99.9999 | About 99.9999 | About 99.999 | About 99.999 |
| 12 | Peroxyacetic acid/about 125 ppm | About 99.9999 | About 99.9999 | About 99.9999 | About 99.9999 | <99 | About 99.99 |

***The data from Examples 7–9 show the percent bacteria killed after the CIP composition and bacteria were combined for 30 seconds and the data from Examples 10–12 show the percent bacteria killed after the CIP composition and bacteria were combined for 2 minutes.
**Examples 7–12 were conducted in the following manner.

Number of Microbes in the Inoculum

American Type Culture Collection cultures were transferred daily and maintained on agar slants containing the appropriate growth medium[1]. A loopful of the culture was transferred into 10 ml of Butterfield's phosphate buffer pH 7.2 (NutraMax Products, Inc.) and agitated to obtain a homogenous turbid suspension. The actual concentration of

[Number of microbes per ml killed by CIP composition −1/Number of microbes per ml killed by the sanitizer solution]×100   (1)

Number of microbes per ml killed by CIP composition=Number of microbes in 0.1 ml of inoculum×10−Number of microbes in 0.1 ml×10 that survived in the CIP composition.   (2)

| [1]Growth Media | | | | | |
| --- | --- | --- | --- | --- | --- |
| Lactobacillus brevis | Bacillus cerus | Candida albicans | Zygosaccharomyces bailii | Rhizopus stolonifer | Byssochlamys nivea |
| Nutrient Agar | Nutrient Agar | YM Agar | YM Agar | Malt Extract Agar | Malt Extract Agar |

| [2]Neutralizer Composition: | |
| --- | --- |
| Lecithin | 6.0 g |
| NIH thioglycollate | 1.0 g |
| Histidine | 2.0 g |
| Phosphate buffer 0.25N | 20.0 ml |
| Na thiosulfate | 2.0 g |
| Tween 80 | 30.0 ml |
| d.i. water | balance to 1 L |

Starting from left to right in Table II, the 6 suspensions had a concentration of 8.2, 8.5, 8.0, 8.5, 7.5 and 8.1 log bacteria/mL, respectively. One (1) mL of suspension and 9.0 mL of CIP composition were combined, resulting in the above data. The pH of the chlorine dioxide CIP composition was 5.8, the mixed halogen is sold by DiverseyLever under the name of Divosan MH and the peroxyacetic acid was an aqueous solution having about 65% water.

The data in Table II demonstrates that the CIP compositions with halogen dioxides unexpectedly result in superior disinfecting properties when significantly less active is used, even in a CIP process.

We claim:

1. A method for cleaning and/or disinfecting food processing equipment, the method comprising the steps of:
   (a) delivering an aqueous liquid cleaning-in-place composition in the absence of a detergent to the processing equipment at a linear velocity from about 1.5 to about 2.5 meters per second through a conduit having an inside diameter from about 0.25 cm to about 20 cm thereby allowing for cleaning and/or disinfecting the food processing equipment; and
   (b) removing the composition from the food processing equipment,
   wherein the composition is an aqueous solution comprising
      a halogen dioxide, the halogen dioxide being derived from a precursor alkali metal halite or alkaline earth metal halite, or both, the food processing equipment being brewery equipment, dairy equipment or carbonated beverage plant equipment.
      a halogen dioxide, the halogen dioxide being derived from a precursor alkali metal halite or alkaline earth metal halite, or both.

2. A method for cleaning and disinfecting processing equipment according to claim 1 wherein the halogen dioxide is fluorine dioxide, chlorine dioxide or a mixture thereof.

3. A method for cleaning and disinfecting processing equipment according to claim 1 wherein the halogen dioxide is a chlorine dioxide.

4. A method for cleaning and disinfecting processing equipment according to claim 1 wherein the composition further comprises a hydroxide wherein the hydroxide is sodium hydroxide.

5. A method for cleaning and disinfecting processing equipment according to claim 1 wherein the composition is delivered by pumping or spraying the composition to the processing equipment.

6. A method for cleaning and disinfecting processing equipment according to claim 1 wherein the composition is:
   (a) generated directly before delivery to the processing equipment, or
   (b) generated, then stored, then delivered to the processing equipment, or
   (c) both.

* * * * *

UNITED STATES PATENT AND TRADEMARK OFFICE
CERTIFICATE OF CORRECTION

PATENT NO. : 6,423,675 B1
DATED : July 23, 2002
INVENTOR(S) : Michael Francis Coughlin et al.

It is certified that error appears in the above-identified patent and that said Letters Patent is hereby corrected as shown below:

Column 8,
Line 22, delete last paragraph of Claim 1.

Signed and Sealed this

Tenth Day of January, 2006

JON W. DUDAS
*Director of the United States Patent and Trademark Office*